United States Patent
Lee et al.

(10) Patent No.: US 9,730,669 B2
(45) Date of Patent: Aug. 15, 2017

(54) X-RAY IMAGING APPARATUS AND CONTROL METHOD THEREOF

(71) Applicant: SAMSUNG ELECTRONICS CO., LTD., Suwon-si (KR)

(72) Inventors: Jong Ha Lee, Hwaseong-si (KR); Sung Hoon Kang, Suwon-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 353 days.

(21) Appl. No.: 14/313,164

(22) Filed: Jun. 24, 2014

(65) Prior Publication Data

US 2015/0063545 A1    Mar. 5, 2015

(30) Foreign Application Priority Data

Aug. 29, 2013 (KR) .................. 10-2013-0102832

(51) Int. Cl.

| | |
|---|---|
| *A61B 6/00* | (2006.01) |
| *G06F 19/00* | (2011.01) |
| *A61B 6/02* | (2006.01) |
| *A61B 6/04* | (2006.01) |

(52) U.S. Cl.
CPC ............ *A61B 6/545* (2013.01); *G06F 19/321* (2013.01); *A61B 6/025* (2013.01); *A61B 6/0407* (2013.01); *A61B 6/466* (2013.01); *A61B 6/467* (2013.01); *A61B 6/502* (2013.01); *A61B 6/5294* (2013.01); *A61B 6/544* (2013.01)

(58) Field of Classification Search
CPC ........ G01N 23/04; A61B 6/06; A61B 6/4233; A61B 6/467; A61B 6/5205; A61B 6/5294; A61B 6/545
See application file for complete search history.

(56) References Cited

U.S. PATENT DOCUMENTS

| | | | | |
|---|---|---|---|---|
| 7,298,823 | B2 * | 11/2007 | Bernhardt | A61B 6/4035 378/97 |
| 7,672,491 | B2 * | 3/2010 | Krishnan | G06T 7/0012 378/21 |
| 2006/0010090 | A1 | 1/2006 | Brockway et al. | |
| 2010/0054417 | A1 * | 3/2010 | Nishino | A61B 6/00 378/98.8 |
| 2011/0110496 | A1 * | 5/2011 | Foos | A61B 6/4405 378/98.5 |
| 2012/0140894 | A1 | 6/2012 | Feuerlein et al. | |
| 2012/0150520 | A1 | 6/2012 | Vaillant et al. | |
| 2012/0155609 | A1 | 6/2012 | Lemminger et al. | |

FOREIGN PATENT DOCUMENTS

| | | |
|---|---|---|
| JP | 2010-264234 A | 11/2010 |
| KR | 10-1050769 B1 | 7/2011 |
| KR | 10-2012-0072961 A | 7/2012 |

* cited by examiner

*Primary Examiner* — Hoon Song
(74) *Attorney, Agent, or Firm* — Sughrue Mion, PLLC

(57) ABSTRACT

Disclosed herein are an X-ray imaging apparatus for optimizing radiography conditions upon radiography, and a control method thereof. The X-ray imaging apparatus includes: an input device configured to receive information about a patient; and a controller configured to conduct a search for a previously obtained X-ray image related to the information about the patient and a previously set radiography condition related to the information about the patient, and to set a radiography condition for a main-shot based on a result of the search.

16 Claims, 14 Drawing Sheets

X-RAY IMAGING APPARATUS AND CONTROL METHOD THEREOF

CROSS-REFERENCE TO RELATED APPLICATION

This application claims priority to Korean Patent Application No. 10-2013-0102832, filed on Aug. 29, 2013 in the Korean Intellectual Property Office, the disclosure of which is incorporated herein by reference in its entirety.

BACKGROUND

1. Field

Exemplary embodiments of the present disclosure relate to an X-ray imaging apparatus for optimizing radiography conditions during radiography, and a control method thereof.

2. Description of the Related Art

An X-ray imaging apparatus is an imaging apparatus for acquiring images about the inside of a subject, such as a human body or another type of object, by irradiating X-rays onto the subject. Since the X-ray imaging apparatus can show the inside structure of an object, the X-ray imaging apparatus is widely used to detect abnormal tissues such as lesions inside a human body at hospitals, or to understand the inside structure of an object or a component. For example, the X-ray imaging apparatus may be used to check the inside of baggage at airports.

The X-ray imaging apparatus may employ many different types of technology, including Digital Radiography (DR), Computed Tomography (CT), and Full Field Digital Mammography (FFDM).

The operation principle of the X-ray imaging apparatus is as follows. The X-ray imaging apparatus irradiates X-rays onto a subject, such as a human body or an object, receives the X-rays transmitted through the subject, converts the received X-rays into electrical signals, and reads out the electrical signals to generate an X-ray image. The X-ray image is displayed by a display unit so that a user can see the inside structure of the subject.

SUMMARY

Therefore, it is an aspect of the exemplary embodiments to provide an X-ray imaging apparatus for optimizing radiography conditions during radiography, and a control method thereof.

Additional aspects of the exemplary embodiments will be set forth in part in the description which follows and, in part, will be obvious from the description, or may be learned by practice of the exemplary embodiments.

In accordance with an aspect of an exemplary embodiment, there is provided an X-ray imaging apparatus including: an input device configured to receive information about a patient; and a controller configured to conduct a search for a previously obtained X-ray image related to the information about the patient and a previously set radiography condition related to the information about the patient, and to set a radiography condition for a main-shot based on a result of the search.

In accordance with another aspect of an exemplary embodiment, there is provided a control method to control an X-ray imaging apparatus including: receiving information about a patient; searching for a previously obtained X-ray image and a previously set radiography condition related to the information about the patient; and setting a radiography condition for a main-shot based on a result of the searching.

Therefore, by setting radiography conditions for a main-shot based on the results of a quality analysis on previously generated X-ray images and previous radiography conditions, it is possible to obtain a high-quality X-ray image for a dose of X-rays irradiated onto an object, or to obtain an X-ray image of the same quality with a lower dose of X-rays.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Figure 1:
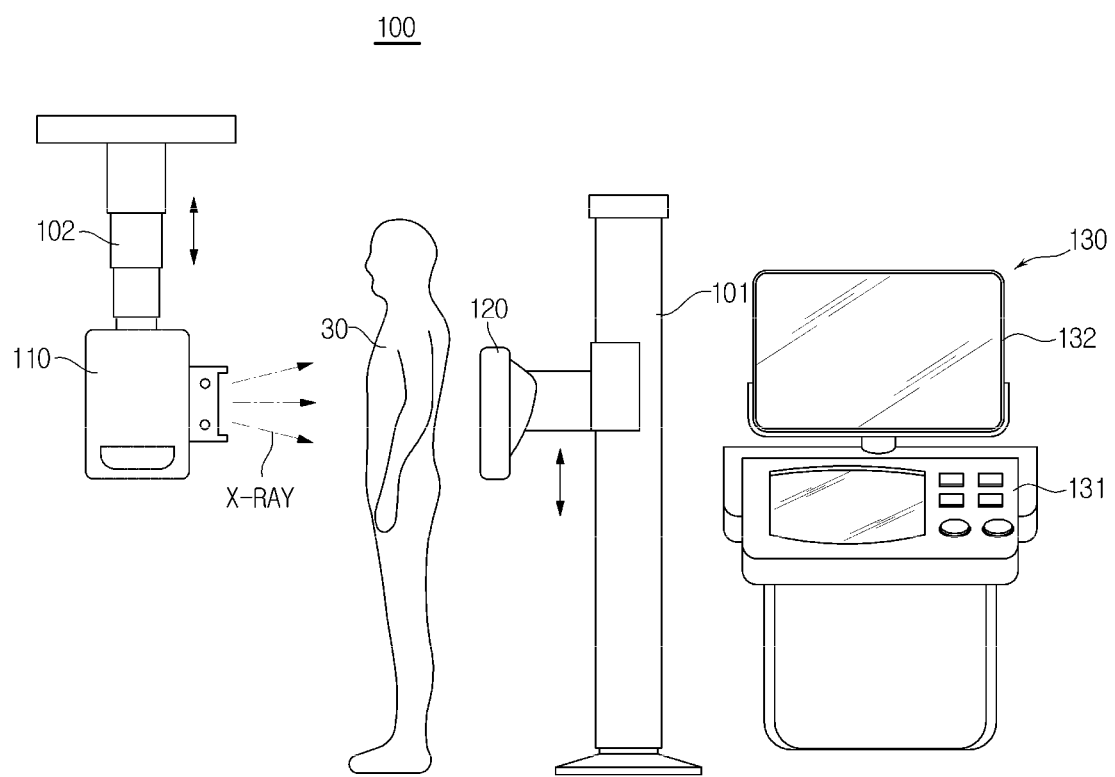
FIG. 1 is a perspective view of an X-ray imaging apparatus according to an exemplary embodiment.

Reference will now be made in detail to the exemplary embodiments, examples of which are illustrated in the accompanying drawings, wherein like reference numerals refer to like elements throughout.

Hereinafter, exemplary embodiments of an X-ray imaging apparatus and a control method thereof will be described with reference to the accompanying drawings.

The X-ray imaging apparatus may employ Digital Radiography (DR). The DR may use an indirect conversion method and a direct conversion method according to a method of detecting X-rays.

In DR using the indirect conversion method, an X-ray detector converts X-rays into light using a scintillator, and detects and reads out the light. The scintillator is disposed between the X-ray detector and a light receiving device, and reacts with X-rays irradiated by an X-ray generator to emit photons having a wavelength of a visible region. The light receiving device detects the photons and converts them into electrical signals. The light receiving device may be made of a-Si. The scintillator may be a thin film type GADOX scintillator or a micro-column type thallium-doped cesium iodide CsI(T1). The micro-column type thallium-doped cesium iodide CsI(T1) may also be referred to as a needle structured type thallium-doped cesium iodide CsI(T1).

The direct conversion method includes the operation of reading out electron-hole pairs generated by direct reaction with X-rays. In DR using the direct conversion method, if X-rays are irradiated, electron-hole pairs are temporarily generated in a light receiving device. Then, due to an electric field applied to both ends of the light receiving device, electrons of the electron-hole pairs move to an anode, and holes of the electron-hole pairs move to a cathode. An X-ray detector converts the movements of the electrons and holes into electrical signals. In the DR using the direct conversion method, the light receiving device may be made of photoconduction materials, such as Amorphous selenium (a-Se), CdZnTe, mercury iodide ($HgI_2$), and lead iodide ($PbI_2$).

The X-ray imaging apparatus according to the current exemplary embodiment may be a general X-ray imaging apparatus or a tomosynthesis X-ray imaging apparatus. The general X-ray imaging apparatus irradiates X-rays onto an object at a predetermined location, and detects the X-rays transmitted through the object to acquire a 2-Dimensional (2D) projection image. Meanwhile, the tomosynthesis X-ray imaging apparatus irradiates X-rays onto an object at different locations, and detects the X-rays transmitted through the object to acquire a plurality of 2D projection images. However, the types of X-ray imaging apparatus according to the exemplary embodiments are not limited to the above-mentioned types of X-ray imaging apparatuses. For example, the X-ray imaging apparatus may be implemented as a tomosynthesis X-ray imaging apparatus but used as a general X-ray imaging apparatus, or may be another type of X-ray imaging apparatus altogether.

The X-ray imaging apparatus may be used to photograph various body parts, for example, a chest, an oral cavity, breasts and bones. Hereinafter, for convenience of description, a part that can be photographed by the X-ray imaging apparatus may also be referred to as an "object". The structure and/or control conditions of the X-ray imaging apparatus may depend on the kinds of objects. Hereinafter, external appearances of X-ray imaging apparatuses according to various exemplary embodiments will be described with reference to FIGS. 1 to 5.

FIG. 1 is a perspective view of an X-ray imaging apparatus according to an exemplary embodiment.

As illustrated in FIG. 1, an X-ray imaging apparatus 100 may include an X-ray generator 110, an X-ray detector 120, and a host apparatus 130.

The X-ray generator 110 may be connected to a holder 102. The holder 102 may be coupled with a rail installed on a ceiling. The holder 102 may move horizontally along the rail. By moving the holder 102 along the rail, the X-ray generator 110 may also move horizontally. Also, the length of the holder 102 may be adjusted in an up-down direction. By adjusting the length of the holder 102 in the up-down direction, the X-ray generator 110 may also move in the up-down direction.

The X-ray detector 120 may be connected to a support 101. The X-ray detector 120 may move in the up-down direction along the support 101.

An object 30 may be placed between the X-ray generator 110 and the X-ray detector 120. If radiography starts, the X-ray generator 110 may move from up to down or from down to up. At this time, the X-ray generator 110 may move automatically or manually under the control of an operator. The operator may be a medical professional, such as a specialist or a doctor. Also, the operator may be a person having an equal qualification to a medical professional, or a licensed person. In a broader sense, according to an exemplary embodiment, the operator may include any type of user who operates the X-ray imaging apparatus.

The X-ray detector 120 may move automatically along with the X-ray generator 110. In other words, during radiography, the X-ray generator 110 and the X-ray detector 120 may move from up to down or from down to up while facing each other with the object 30 in between.

Although not shown in FIG. 1, the X-ray imaging apparatus 100 may further include a location detector for detecting the location of the X-ray generator 110. The location detector may be a camera. In this case, the camera may be installed around the support 101 or the X-ray detector 120 in order to photograph the X-ray generator 110. The location of the X-ray generator 110 may be detected from an image photographed by the camera, and a distance by which the X-ray detector 120 should move may be calculated based on the results of the detection. The X-ray detector 120 may move by the calculated distance, thereby moving along with the X-ray generator 110.

In order to easily detect the location of the X-ray generator 110 from an image photographed by the camera, the X-ray generator 110 may include one or more markers. The markers may have the same shape and/or color, or different shapes and/or colors.

By irradiating X-rays onto the object 30, for example, a person sitting or standing, using the X-ray imaging apparatus 100 as illustrated in FIG. 1, a 2D projection image may be obtained.

The host apparatus 130 may provide a user interface. The host apparatus 130 may include an input unit 131 (e.g., input device) and a display unit 132 (e.g., display).

The input unit 131 may receive an instruction or command for controlling operations of the X-ray imaging apparatus 100 from an operator. For example, the input unit 131 may receive information about a patient from an operator. The information about the patient is information for identifying the patient, and may include the patient's name, the patient's identifier (ID), the patient's phone number, and a combination thereof. The input unit 131 may include at least one of a foot pedal, a keyboard, and a mouse. The foot pedal may be provided under the host apparatus 130. The keyboard may include at least one key and/or at least one knob.

The display unit 132 may display X-ray images acquired by the X-ray imaging apparatus 100. The X-ray images acquired by the X-ray imaging apparatus 100 may include a 2D projection image, a 2D reprojection image, and a 3-Dimensional (3D) stereo image.

According to an exemplary embodiment, the 2D projection image is acquired by irradiating X-rays onto the object 30 and detecting the X-rays transmitted through the object 30. If the X-ray imaging apparatus 100 is a general X-ray imaging apparatus, radiography is performed one time to acquire a 2D projection image. If the X-ray imaging apparatus 100 is a tomosynthesis X-ray imaging apparatus, radiography is performed one time to acquire a plurality of 2D projection images. The 2D reprojection image is acquired by performing volume rendering on 3D volume data reconstructed from a plurality of 2D projection images. The 3D stereo image is acquired by performing volume rendering on 3D volume data at left and right viewpoints respectively to acquire left and right images, and then combining the left image with the right image.

In FIG. 1, the host apparatus 130 includes the single display unit 132. However, the host apparatus 130 may include a plurality of display units 132. For example, the host apparatus 130 may include two display units 132. In this case, one of the two display units 132 may display a plurality of 2D projection images, and the other one of the two display units 132 may display a 2D reprojection image or a 3D stereo image.

As another example, the display unit 132 of the host apparatus 130 may divide a display area into a plurality of sections, and display a 2D projection image, a 2D reprojection image, and a 3D stereo image in the respective sections. Alternatively, whenever an X-ray image is acquired by the X-ray imaging apparatus 100 during radiography, the display unit 132 may display the acquired X-ray image through the display unit 132. At this time, an X-ray image that has been previously displayed may be stored in a storage unit (for example, 160 of FIG. 6), or displayed as an icon in the lower part of a display area.

A type of an X-ray image which may be displayed by the display unit 132 and a method by which the X-ray image may be displayed by the display unit 132 may be decided in advance by the operator. Also, setting values related to a type of an X-ray image which may be displayed by the display unit 132 and a method by which the X-ray image may be displayed by the display unit 132 may be changed by the operator during or after radiography.

Figure 2:
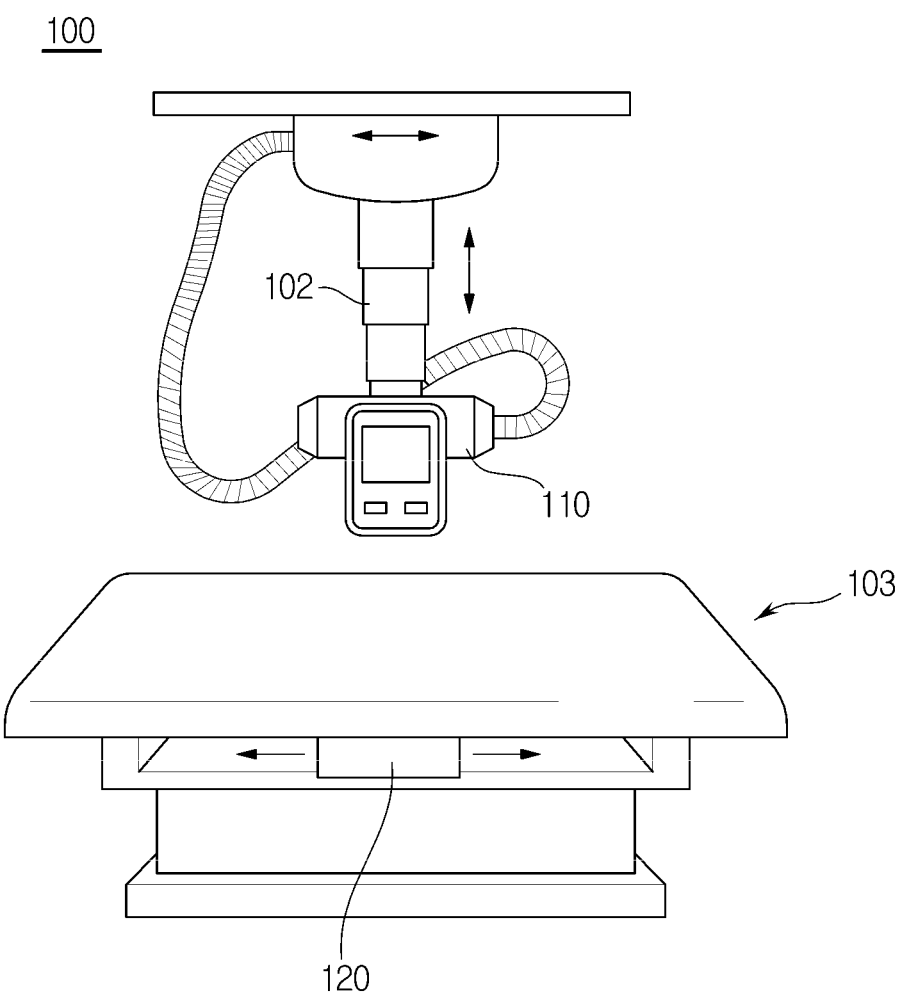
FIG. 2 is a perspective view of an X-ray imaging apparatus according to another exemplary embodiment.

FIG. 2 is a perspective view of an X-ray imaging apparatus according to another exemplary embodiment.

The X-ray imaging apparatus 100 illustrated in FIG. 1 irradiates X-rays onto the object 30, for example, a person sitting or standing, to acquire one or more 2D projection images, whereas the X-ray imaging apparatus 100 illustrated in FIG. 2 irradiates X-rays onto an object 30 which is laid on a table 103 to acquire one or more 2D projection images.

Referring to FIG. 2, similar to the X-ray imaging apparatus of FIG. 1, an X-ray generator 110 may be connected to a ceiling through a holder 102, and the holder 102 may move horizontally along a rail installed on the ceiling. A difference between the X-ray imaging apparatus 100 of FIG. 1 and the X-ray imaging apparatus 100 of FIG. 2 is the table 103 which is provided under the X-ray generator 110. The X-ray detector 120 may be located under the table 103. The X-ray detector 120 may be configured to move horizontally under the table 103.

If radiography starts, the X-ray generator 110 may move horizontally, for example, in the length direction of the table 103. At this time, the X-ray generator 110 may move automatically or manually by an operator. The X-ray detector 120 may move automatically along with the X-ray generator 110. To achieve this synchronized movement, the X-ray imaging apparatus 100 may further include a location detector for detecting a location of the X-ray generator 110.

In FIG. 2, a case in which the X-ray generator 110 and the X-ray detector 120 move in the length direction of the table 103 is illustrated. However, it is understood that the X-ray generator 110 and the X-ray detector 120 may move in other directions, for example, the width direction of the table 103.

Figure 3:
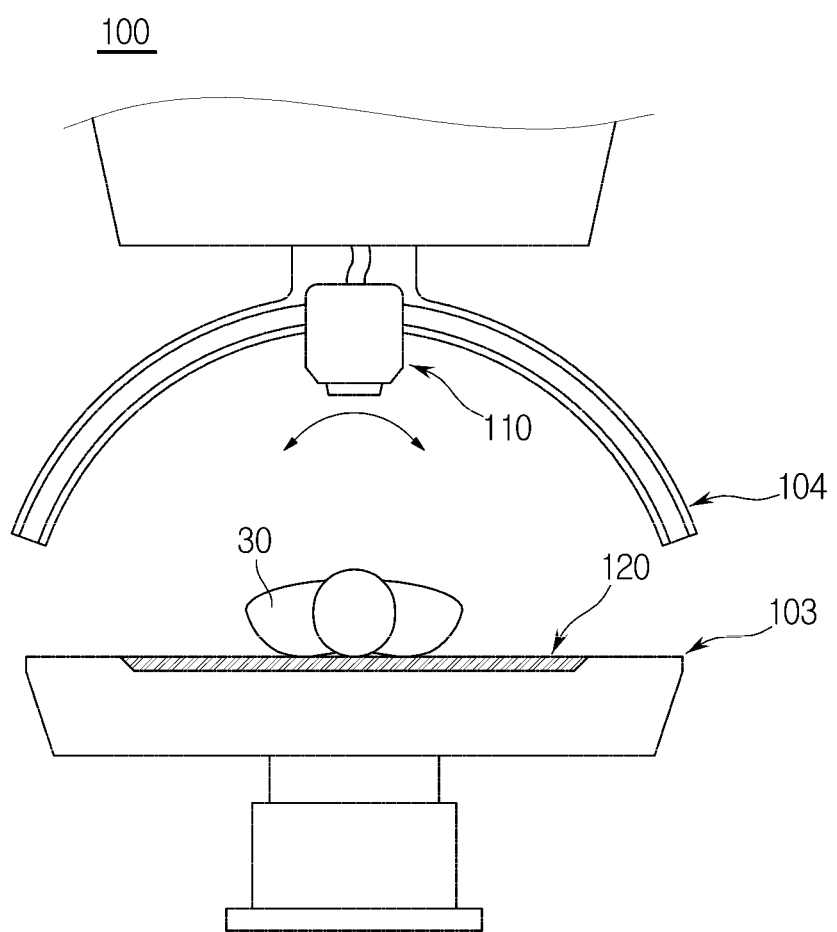
FIG. 3 is a perspective view of an X-ray imaging apparatus according to another exemplary embodiment.

FIG. 3 is a perspective view of an X-ray imaging apparatus according to another exemplary embodiment.

An X-ray imaging apparatus 100 illustrated in FIG. 3 may irradiate X-rays onto an object 30 placed on a table 103 to acquire a 2D projection image of the object 30, similar to the X-ray imaging apparatus 100 illustrated in FIG. 2.

The X-ray imaging apparatus 100 illustrated in FIG. 3 includes the table 103 similar to the X-ray imaging apparatus 100 illustrated in FIG. 2, but unlike the X-ray imaging apparatus 100 illustrated in FIG. 2, also includes a C-arm 104.

An X-ray generator 110 may be provided on the C-arm 104. If radiography starts, the X-ray generator 110 may irradiate X-rays onto the object 30 at different locations while moving along the C-arm 104. An X-ray detector 120 located on the table 103 may be fixed.

In FIG. 3, a case in which the C-arm 104 is fixed and the X-ray detector 120 moves along the C-arm 104 is illustrated. However, other configurations are possible, such as, for example, a configuration in which the X-ray generator 110 may be fixed at the C-arm 104 and the C-arm 104 may move.

Figure 4:
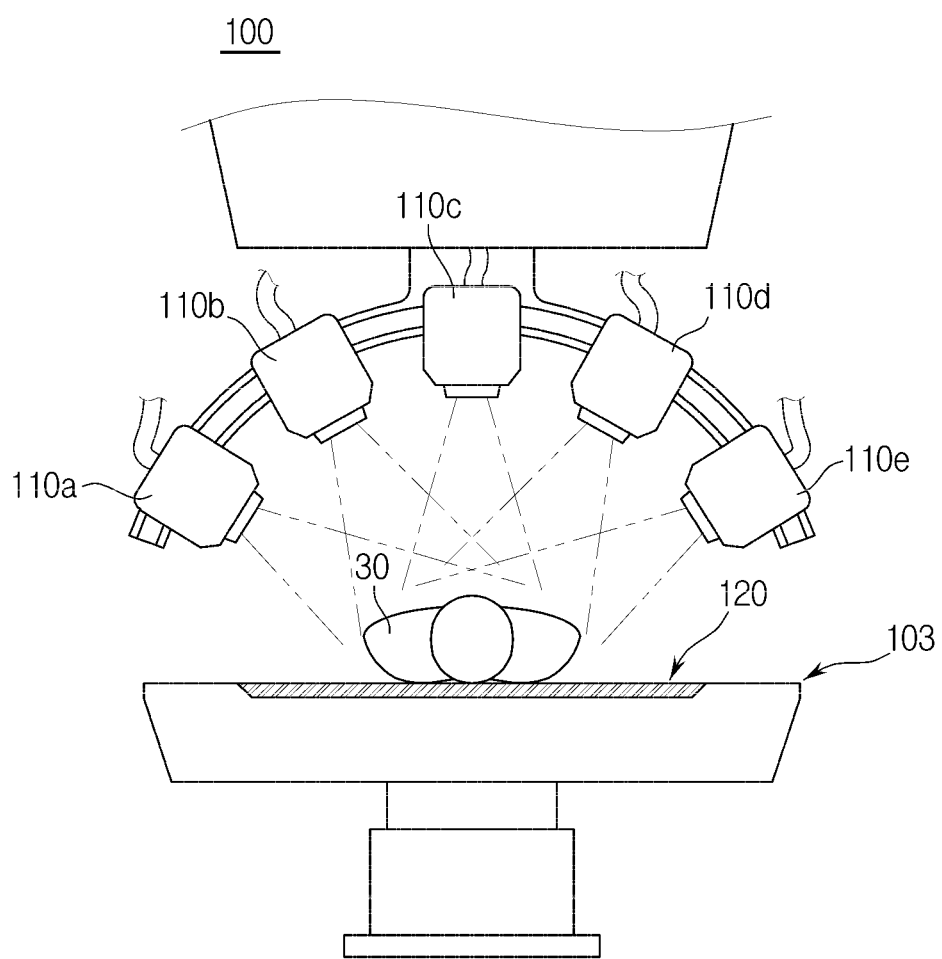
FIG. 4 is a perspective view of an X-ray imaging apparatus according to another exemplary embodiment.

FIG. 4 is a perspective view of an X-ray imaging apparatus according to another exemplary embodiment.

An X-ray imaging apparatus 100 illustrated in FIG. 4 includes a table 103 and a C-arm 104 similar to the X-ray imaging apparatus 100 illustrated in FIG. 3, but unlike the X-ray imaging apparatus 100 illustrated in FIG. 3, also includes a plurality of X-ray generators 110a, 110b, 110c, 110d, and 110e on the C-arm 104.

If radiography starts, the plurality of X-ray generators 110a to 110e may irradiate X-rays onto an object 30 simultaneously or sequentially. An X-ray detector 120 located on the table 103 may be fixed.

Since the X-ray imaging apparatus 100 illustrated in FIG. 3 or the X-ray imaging apparatus 100 illustrated in FIG. 4 can irradiate X-rays onto the object 30 at different locations, X-ray images photographed at different angles may be acquired.

In FIGS. 3 and 4, a case in which the X-ray detector 120 is fixed regardless of the location of the X-ray generator 110 (or the X-ray generators 110a to 110e) is illustrated. However, the X-ray detector 120 may move along with the X-ray generator 110 while facing the X-ray generator 110.

Figure 5:
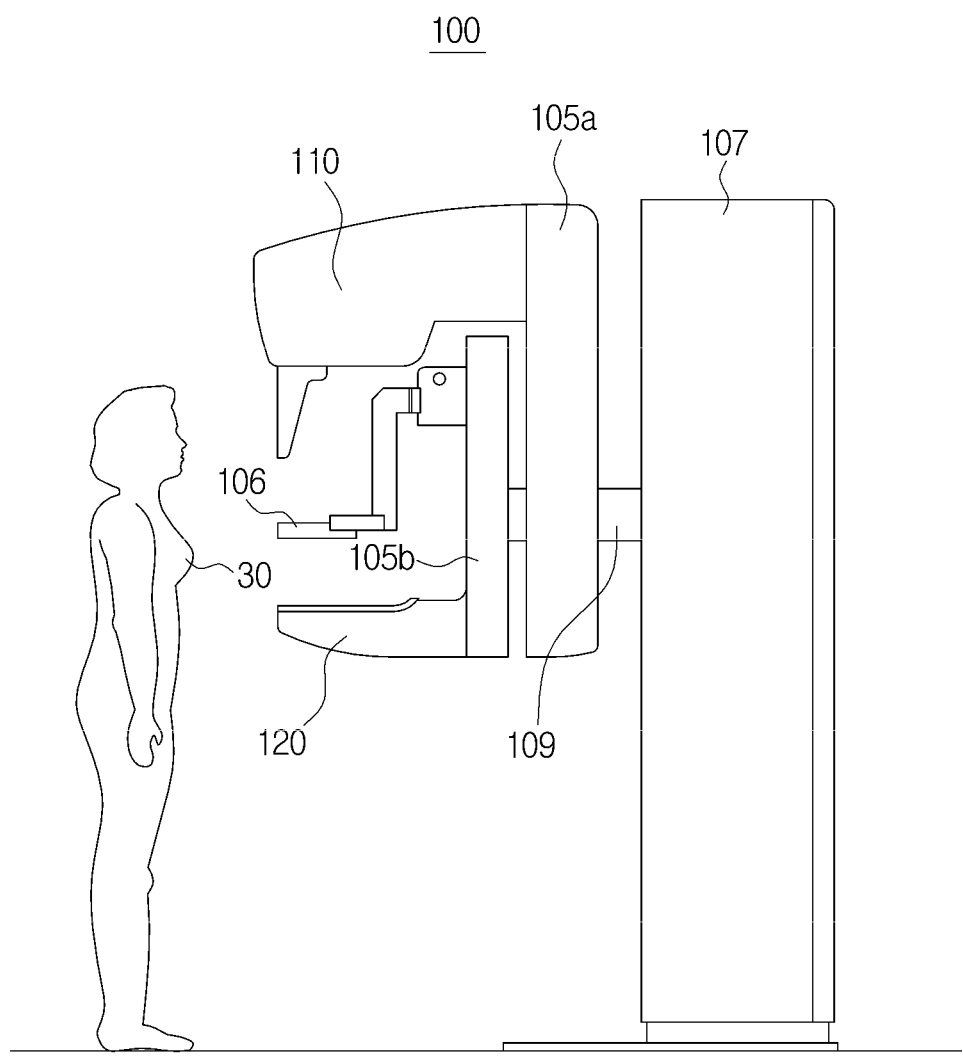
FIG. 5 is a perspective view of an X-ray imaging apparatus according to another exemplary embodiment.

FIG. 5 is a perspective view of an X-ray imaging apparatus according to another exemplary embodiment.

An X-ray imaging apparatus 100 illustrated in FIG. 5 is used to take X-ray images of a breast 30, and includes a pressure paddle 106 for pressing the breast 30. Since the breast 30 is configured with only soft tissue, the breast 30 must be subject to X-ray irradiation after being pressed by the pressure paddle 106 in order to obtain a clear X-ray image.

If the breast 30 is located on the X-ray detector 120, the pressure paddle 106 may move downward to press the breast 30 to a predetermined thickness. At this time, the pressure paddle 106 may move manually by an operator or automatically by a driver (not shown) such as a motor. The driver may be driven according to an instruction or command input by the operator.

If the breast 30 is pressed by the pressure paddle, a first arm 105a including an X-ray generator 110 may be rotated to predetermined angles with respect to a connection axis connected to a housing 107 so as to irradiate X-rays onto the breast 30 at the predetermined angles. At this time, the X-ray detector 120 may rotate along with the X-ray generator 110 or may be fixed.

If X-rays are irradiated onto the breast 30, the X-ray detector 120 may detect the X-rays transmitted through the breast 30. Although not shown in FIG. 5, a grid may be provided between the breast 30 and the X-ray detector 120. The grid may remove scattered X-rays among the X-rays transmitted through the breast 30 so that only X-rays having straightness can be detected by the X-ray detector 120.

External appearances of X-ray imaging apparatuses according to various exemplary embodiments have been described with reference to FIGS. 1 to 5. Hereinafter, a control configuration of the X-ray imaging apparatus 100 will be described.

Figure 6:
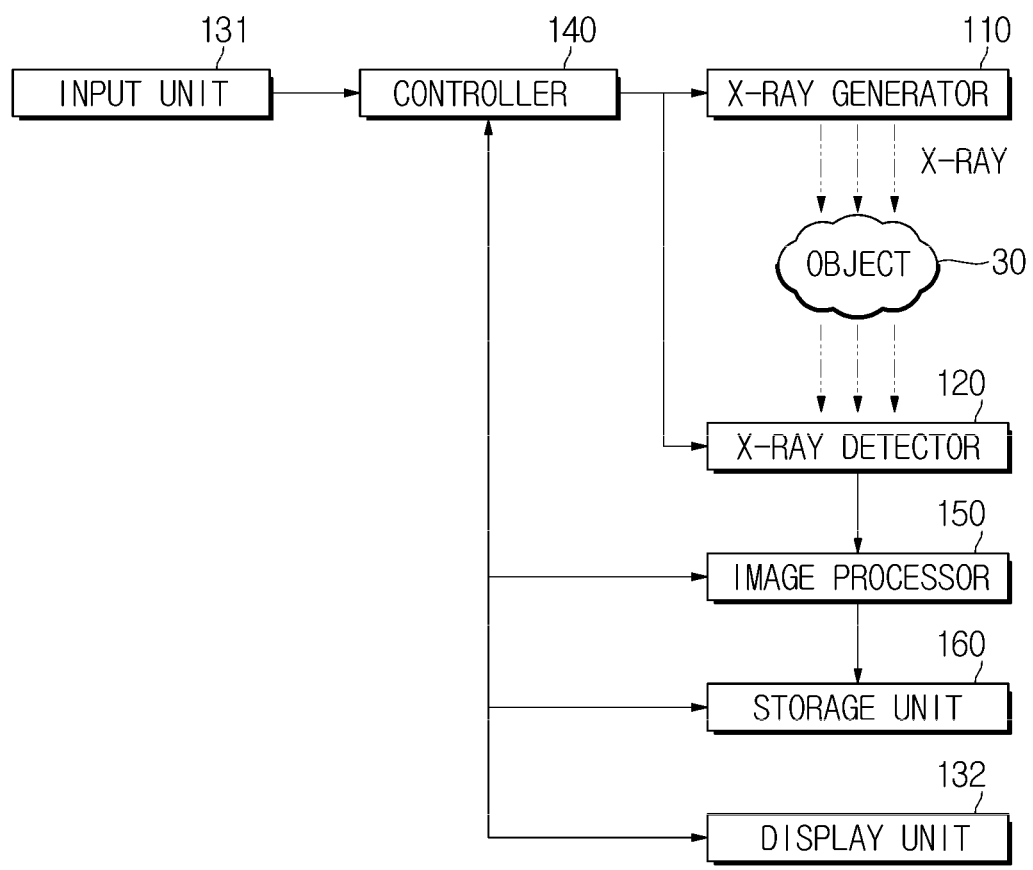
FIG. 6 is a block diagram of a control configuration of an X-ray imaging apparatus according to an exemplary embodiment.

FIG. 6 is a block diagram of a control configuration of an X-ray imaging apparatus according to an exemplary embodiment.

As illustrated in FIG. 6, an X-ray imaging apparatus 100 may include an input unit 131, a display unit 132, an X-ray generator 110, an X-ray detector 120, a controller 140, an image processor 150, and a storage unit 160.

The input unit 131 and the display unit 132 have been described above with reference to FIG. 1, and accordingly, detailed descriptions thereof will be omitted.

The X-ray generator 110 may generate X-rays and irradiate the X-rays onto an object 30. The X-ray generator 110 may include an X-ray tube 111 to generate X-rays. The X-ray tube 111 will be described in more detail with reference to FIG. 7, below.

Figure 7:
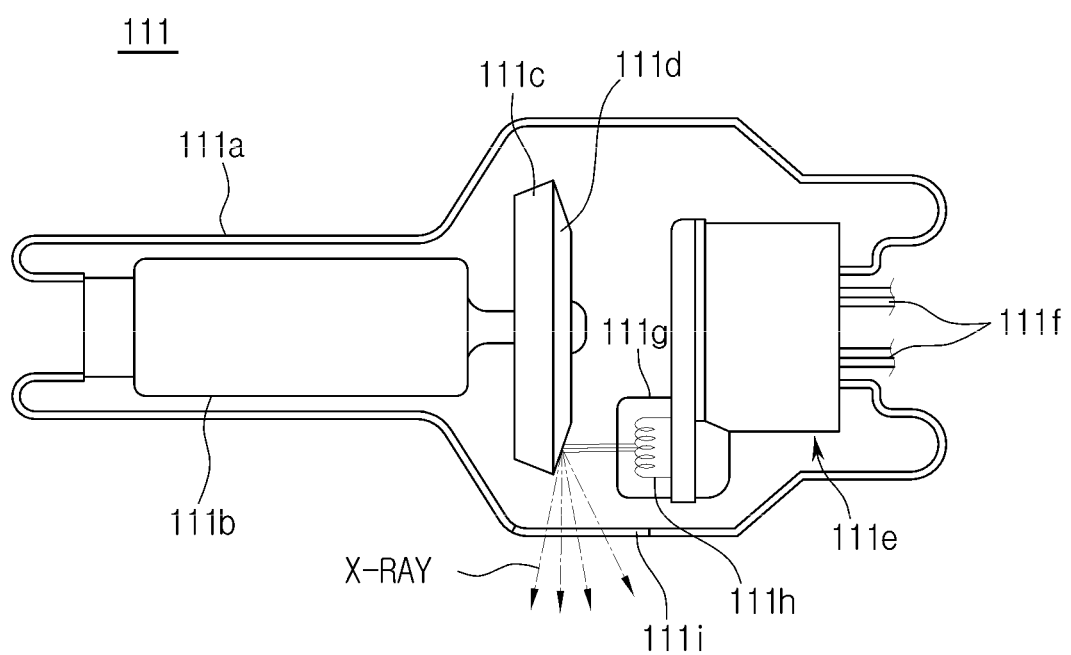
FIG. 7 schematically illustrates a structure of an X-ray tube included in an X-ray generator.

FIG. 7 schematically illustrates a structure of the X-ray tube 111 included in the X-ray generator 110.

Referring to FIG. 7, the X-ray tube 111 may be embodied as a two-electrode vacuum tube including an anode 111c and a cathode 111e. The body of the two-electrode vacuum tube may be a glass tube 111a made of silica (hard) glass or the like.

The cathode 111e includes a filament 111h and a focusing electrode 111g for focusing electrons, and the focusing electrode 111g may also be referred to as a focusing cup. The inside of the glass tube 111a is evacuated to a high vacuum state of about 10 mmHg, and the filament 111h of the cathode 111e is heated to a high temperature, thereby generating thermoelectrons. The filament 111h may be a tungsten filament, and the filament 111h may be heated by applying a current to electrical leads 111f connected to the filament 111h. However, instead of the filament 111h, a carbon nano-tube capable of being driven with high-speed pulses may be used as the cathode 111e.

The anode 111c may be made of copper, and a target material 111d is applied on the surface of the anode 111c facing the cathode 111e, wherein the target material 111d may be a high-Z material, e.g., Cr, Fe, Co, Ni, W, or Mo. The higher the melting point of the target material 111d, the smaller the focal spot size.

When a high voltage is applied between the cathode 111e and the anode 111c, thermoelectrons are accelerated and collide with the target material 111d of the anode 111e, thereby generating X-rays. The X-rays are irradiated to the outside through a window 111i. The window 111i may be a Beryllium (Be) thin film. A filter (not shown) may be provided on the front or rear surface of the window 111i to filter out a specific energy band of X-rays.

The target material 111d may be rotated by a rotor 111b. When the target material 111d rotates, the heat accumulation rate may increase 10 times per unit area and the focal spot size may be reduced, compared to when the target material 111d is fixed.

The voltage that is applied between the cathode 111e and the anode 111c of the X-ray tube 111 may be referred to as a tube voltage. The magnitude of a tube voltage may be expressed as a crest value (kVp).

When the tube voltage increases, a velocity of thermoelectrons increases accordingly. Then, the energy of the X-rays (energy of photons) that are generated when the thermoelectrons collide with the target material 111d also increases. When the energy of the X-rays increases, an amount of the X-rays transmitted through an object increases accordingly. When the amount of the X-rays transmitted through the object increases, an amount of X-rays that are detected by the X-ray detector 120 also increases. As a result, a 2D projection image having a high signal-to-noise ratio (SNR), that is, a high-quality 2D projection image, may be acquired.

In contrast, when the tube voltage decreases, a velocity of the thermoelectrons decreases, so that the energy of X-rays that are generated when the thermoelectrons collide with the target material 111d also decreases. When the energy of the X-rays decreases, an amount of the X-rays absorbed in an object increases, and an amount of the X-rays that are detected by the X-ray detector 120 decreases accordingly. As a result, an image having a low SNR, that is, a low-quality 2D projection image, may be acquired.

A current flowing through the X-ray tube 111 may be referred to as a tube current, and can be expressed as an average value (mA). When a tube current increases, a dose of X-rays (that is, the number of X-ray photons) increases, so that a 2D projection image having a high SNR is acquired. In contrast, when a tube current decreases, a 2D projection image having a low SNR is acquired.

In summary, an energy level of X-rays can be controlled by adjusting a tube voltage. Also, a dose or intensity of X-rays can be controlled by adjusting a tube current and an X-ray exposure time. Accordingly, by controlling a tube voltage and a tube current according to the kind or properties of an object, it is possible to control the energy level and intensity of X-rays that are irradiated.

X-rays that are irradiated from the X-ray source 110 have a predetermined energy band. The predetermined energy band may be defined by upper and lower limits. The upper limit of the predetermined energy band, that is, a maximum energy of X-rays to be irradiated, may be adjusted by the magnitude of a tube voltage, and the lower limit of the predetermined energy band, that is, a minimum energy of X-rays to be irradiated, may be adjusted by a filter (not shown) included in or provided outside the X-ray source 110. By filtering out a low energy band of X-ray beams using the filter, an average energy of X-rays to be irradiated may increase. The energy of X-rays that are irradiated may be expressed as a maximum energy or an average energy.

Referring again to FIG. 6, the X-ray detector 120 may detect X-rays transmitted through the object 30, and convert the X-rays into electrical signals. The X-ray detector 120 will be described in more detail with reference to FIG. 8, below.

Figure 8:
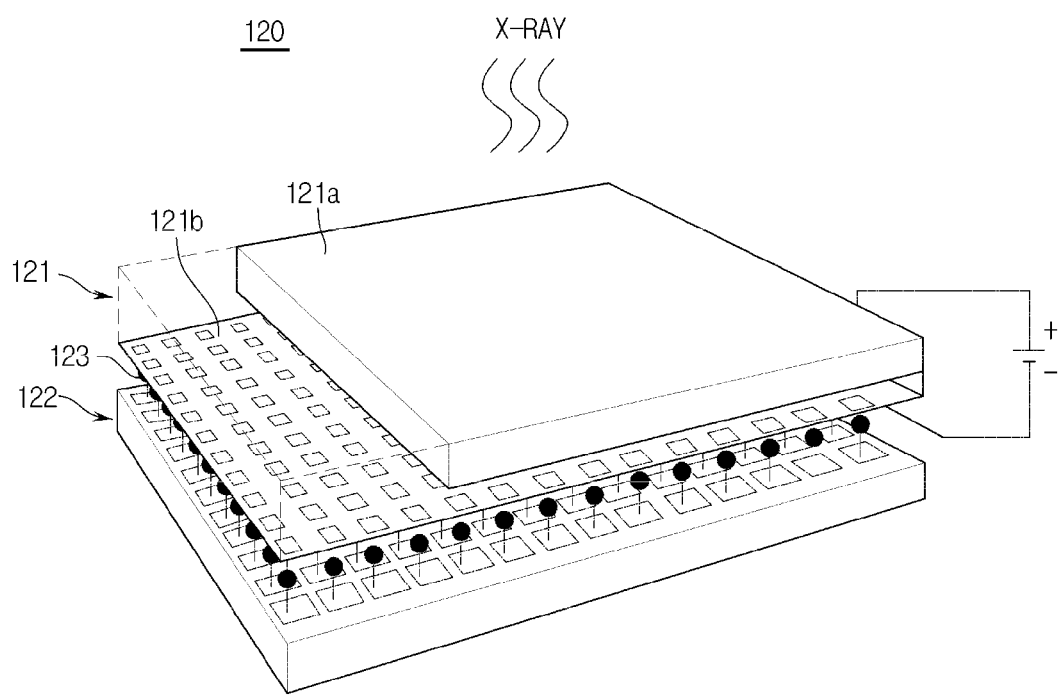
FIG. 8 schematically illustrates a structure of an X-ray detector.

FIG. 8 schematically illustrates a structure of the X-ray detector 120.

Referring to FIG. 8, the X-ray detector 120 may include a light receiving device 121 to detect X-rays and convert the X-rays into electrical signals, and a read circuit 122 to read out the electrical signals from the light receiving device 121. The read circuit 122 is in the form of a 2-dimensional (2D) pixel array including a plurality of pixel areas. The light receiving device 121 may be made of a single crystal semiconductor material in order to ensure high resolution, a high response speed, and a high dynamic area even under conditions of low energy and a small dose of X-rays. The single crystal semiconductor material may be Ge, CdTe, CdZnTe, or GaAs.

The light receiving device 121 may be in the form of a PIN photodiode. The PIN photodiode is fabricated by bonding a p-type layer 121b in which p-type semiconductors are arranged in the form of a 2D pixel array on the lower surface of an n-type semiconductor substrate 121a having a high resistance. The read circuit 122, which is fabricated according to a CMOS process, is coupled with the light receiving device 121 in units of pixels. The CMOS read circuit 122 and the light receiving device 121 may be coupled by a Flip-Chip Bonding (FCB) method. More specifically, the CMOS read circuit 122 and the light receiving device 121 may be coupled by forming bumps 123 with PbSn, In, or the like, reflowing, applying heat, and then compressing. However, the X-ray detector 120 is not limited to this structure.

Referring again to FIG. 6, the image processor 150 may produce a 2D projection image based on electrical signals output from individual pixels of the X-ray detector 120.

For example, if the X-ray generator 110 irradiates X-rays onto an object 30 at a predetermined location, the image processor 150 may generate a 2D projection image corresponding to the location of the X-ray generator 110.

As another example, if the X-ray generator 110 irradiates X-rays onto the object 30 at different locations, the image processor 150 may generate 2D projection images corresponding to the respective locations of the X-ray generator 110. If a plurality of 2D projection images is acquired, the image processor 150 may perform image reconstruction on the plurality of 2D projection images to obtain 3D volume data.

Then, the image processor 150 may perform quality analysis on at least one of a 2D projection image, a 2D reprojection image, and 3D volume data. The image processor 150 will be described in more detail with reference to FIG. 9, below.

Figure 9:
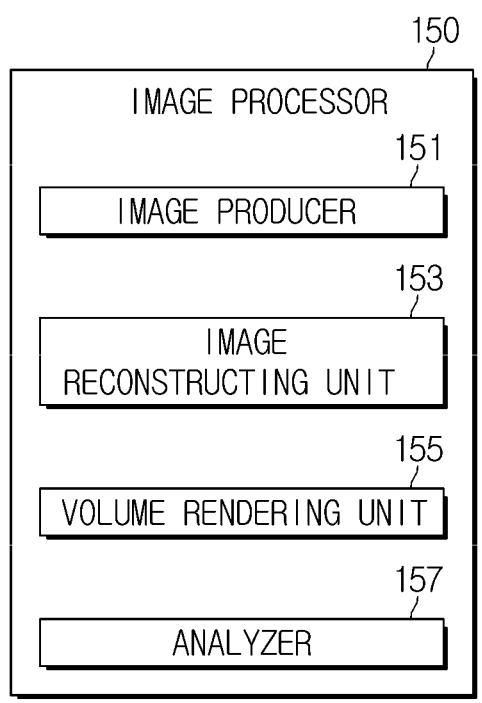
FIG. 9 is a block diagram of an image processor.

FIG. 9 is a block diagram of the image processor 150.

Referring to FIGS. 6 and 9, the image processor 150 may include an image producer 151, an image reconstructing unit 153, a volume rendering unit 155, and an analyzer 157.

The image producer 151 may produce (e.g., generate) a 2D projection image based on electrical signals output from individual pixels of the X-ray detector 120. In a general X-ray imaging apparatus, the image producer 151 may generate a single 2D projection image. In a tomosynthesis X-ray imaging apparatus, the image producer 151 may generate a plurality of 2D projection images. The plurality of 2D projection images may be stored in the storage unit 160 which will be described later, or may be provided to the image reconstructing unit 153.

The image reconstructing unit 153 may perform image reconstruction on a plurality of 2D projection images. Image reconstruction is an operation to reconstruct an object, represented two-dimensionally in each 2D projection image, three-dimensionally so that the object is shown similar to a real object. Image reconstruction methods include an iterative method, a non-iterative method, a direct Fourier method, and a back projection method.

The iterative method continuously corrects a 2D projection image of an object until data capable of representing a structure similar to a real structure of the object is obtained. The non-iterative method applies an inverse-transform function of a transform function used to model a 3D object to a 2D image to a plurality of X-ray images, thereby three-dimensionally reconstructing an object represented two-dimensionally. An example of the non-iterative method is Filtered Back-projection. The Filtered Back-projection performs filtering in order to cancel a blur formed around the center of an X-ray image, and then performs back projection. The direct Fourier method converts an X-ray image from the spatial domain to the frequency domain. The back projection method returns X-ray images acquired at a plurality of viewpoints to one screen.

The image reconstructing unit 153 may perform image reconstruction using one of the above-mentioned methods, and acquire 3D volume data as the result of the image reconstruction. The 3D volume data may be represented as a plurality of voxels. If a pixel defines a point on a 2D plane, a voxel defines a point in a 3D space. That is, a pixel includes x- and y-coordinates, whereas a voxel includes x-, y-, and z-coordinates.

The volume rendering unit 155 may perform volume rendering on the 3D volume data. Volume rendering is an operation to project 3D volume data onto a 2D plane with respect to a predetermined viewpoint. The volume rendering may be classified into surface rendering and direct volume rendering.

Surface rendering extracts surface information from volume data based on predetermined scalar values and amounts of spatial changes, converts the surface information into a geometric factor, such as a polygon or a curved patch, and then applies a conventional rendering technique to the geometric factor. Examples of surface rendering include a marching cubes algorithm and a dividing cubes algorithm.

Direct volume rendering directly renders volume data without converting volume data into a geometric factor. Direct volume rendering is useful to represent a translucent structure since direct volume rendering can visualize the inside of an object as the inside actually appears. Direct volume rendering may be classified into an object-order method and an image-order method according to a way of approaching volume data.

The object-order method searches for volume data in a storage order and synthesizes each voxel with the corresponding pixel value. A representative example of the object-order method is splatting.

The image-order method sequentially decides pixel values in the order of scan lines of an image. Examples of the image-order method are Ray-Casting and Ray-Tracing.

Figure 10:
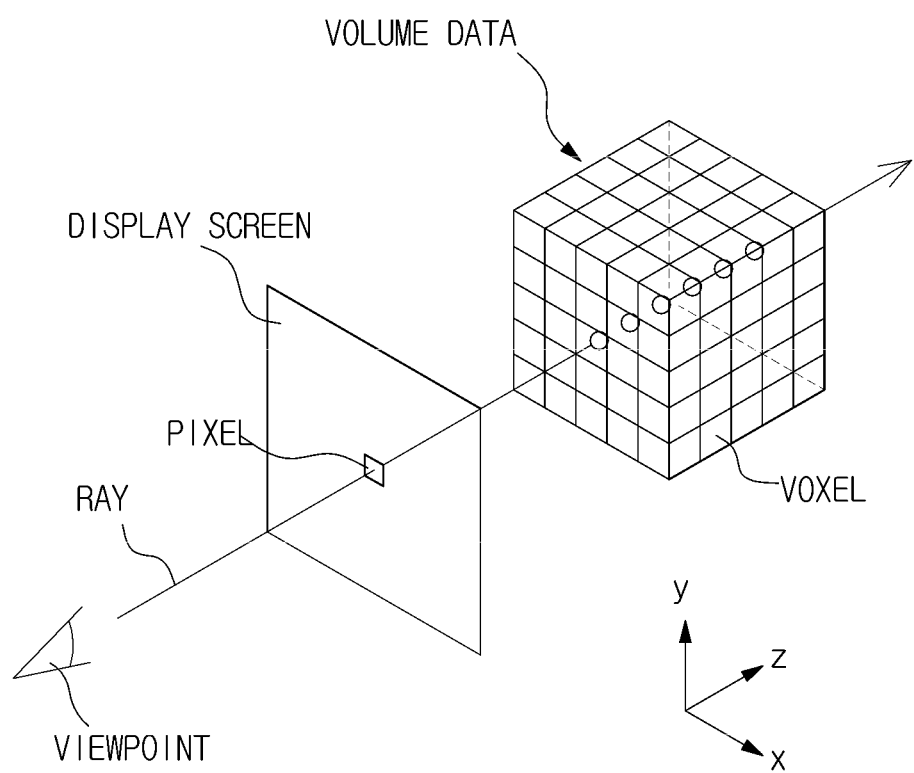
FIG. 10 is a view illustrating Ray-casting among volume rendering methods.

Ray-Casting is, as illustrated in FIG. 10, a technique of irradiating a virtual ray from a specific viewpoint toward a predetermined pixel of a display screen, and detecting voxels through which the virtual ray has been transmitted from among voxels of volume data. Then, brightness values of the detected voxels are accumulated to decide a brightness value of the corresponding pixel of the display screen. Alternatively, an average value of the detected voxels may be decided as a brightness value of the corresponding pixel of the display screen. Also, a weighted average value of the detected voxels may be decided as a brightness value of the corresponding pixel of the display screen.

Ray-Tracing is a technique of tracing a path of a ray headed towards an observer's eyes. Unlike the Ray-Casting technique of detecting an intersection at which a ray meets volume data, the Ray-Tracing technique can trace an irradiated ray and thereby reflect how the ray travels, such as reflection, refraction, etc. of the ray.

Ray-Tracing can be classified into Forward Ray-Tracing and Backward Ray-Tracing. Forward Ray-Tracing models a phenomenon in which a ray irradiated from a virtual light source arrives at volume data to be reflected, scattered, or transmitted, thereby finding a ray finally coming to an observer's eyes. Backward Ray-Tracing backwardly traces a path of a ray headed towards an observer's eyes.

Referring again to FIG. 9, the volume rendering unit 155 may perform volume rendering on the 3D volume data using one of the above-mentioned volume rendering methods. If the 3D volume data is subject to volume rendering with respect to a viewpoint, a 2D reprojection image may be acquired. If the 3D volume data is subject to volume rendering with respect to two viewpoints respectively corresponding to a human's left and right eyes, left and right images may be acquired. The left image is combined with the right image, thereby acquiring a 3D stereo image. The 2D reprojection image or the 3D stereo image acquired as the results of the volume rendering may be displayed through the display unit 132.

The analyzer 157 may analyze the quality of an X-ray image acquired by the X-ray imaging apparatus 100.

For example, the analyzer 157 may analyze the quality of at least one image among a plurality of 2D projection images and a 2D reprojection image acquired as the results of the volume rendering. As criterion for determining the quality of an X-ray image, contrast, spatial resolution, a Signal-to-Noise Ratio (SNR), a Noise Power Spectrum (NPS), a Modulation Transfer Function (MTF), and a Detective Quantum Efficiency (DQE) may be used.

Contrast is an index to represent a difference in optical density (that is, a brightness difference) of two areas adjacent to each other in an X-ray image. As two areas are located closer to each other, the contrast becomes smaller. Contrast is defined as $\Delta\phi/\phi 1$ ($\Delta\phi 1=\phi 1-\phi 2$), wherein "$\phi 1$" represents X-ray fluence (that is, the number of X-ray photons) of a background area in the X-ray image, and "$\phi 2$" represents X-ray fluence of an object area in the X-ray image. The contrast is reduced as the magnitude of the object is reduced.

Spatial resolution is an index to represent a minimum distance between two objects that can be distinguished in an X-ray image. When a distance between the two objects is short, blurring occurs in the X-ray image. Blurring may be represented by a Point Spread Function (PSF), a Line Spread Function (LSF), or an Edge Spread Function (ESF).

SNR (signal-to-noise ration) is an index to represent an effect of noise with respect to a finally detected image signal, wherein the noise is a concept representing uncertainity or inaccuracy of the image signal. SNR is represented as a ratio of noise to an image signal ($SNR=\Delta D/\sigma$). Here, $\Delta D=D2-D1$, wherein "D2" represents an image signal of an object area in an X-ray image, "D1" represents an image signal of a background area in the X-ray image, and "$\sigma$" represents noise included in the image signal of the object area. The noise is represented as standard deviation of the image signal of the object area. The noise of the X-ray image is influenced by the number of photons. If the number of photons is small, a probability that the photons will be detected as an image signal becomes low, so that influence of noise on an image signal increases. In contrast, if the number of photons increases, a probability that the photons will be detected as an image signal increases accordingly, so that influence of noise on an image signal decreases.

NPS (noise power spectrum) represents the fluctuation and amplitude of noise as a frequency function. The NPS is also called a Wiener spectrum.

MTF (modulation transfer function) is an index to represent a transfer characteristic of contrast according to spatial resolution. The MTF represents how efficiently contrasts of objects (or lesions) having various sizes are imaged. The MTF can be obtained by performing Fourier Transform on a Contrast Transfer Function (CTF). The CTF is obtained by expressing a contrast as a spatial frequency function.

DQE (detective quantum efficiency) is an index in which the concept of a dose of radiation is included in a relationship of sharpness and noise. If the number of X-ray quanta is insufficient while an X-ray image is generated, signal variations become significant in the X-ray image, which is called quantum noise. The DQE is defined as a ratio of $SNR^2$ at an input terminal of the X-ray detector 120 to $SNR^2$ at an output terminal of the X-ray detector 120 ($DQE=SNR_{out}^2/SNR_{input}^2$). A high DQE indicates that an X-ray image having high sharpness and low noise can be acquired with a low dose of radiation.

As another example, the analyzer 157 may analyze the quality of the 3D volume data acquired as the result of the image reconstruction. More specifically, the analyzer 157 may analyze the frequency of the 3D volume data.

Referring again to FIG. 6, the storage unit 160 may store data used to operate the X-ray imaging apparatus 100 and/or data generated by the X-ray imaging apparatus 100.

For example, the storage unit 160 may store radiography conditions of the X-ray imaging apparatus 100, and X-ray images (e.g., 2D projection images and 2D reprojection images) acquired according to the radiography conditions.

When an object is photographed at different times, radiography conditions and X-ray images acquired according to the radiography conditions may be stored in order of time in the storage unit 160. At this time, the radiography conditions and the X-ray images may be stored together with information about a patient. The stored radiography conditions and X-ray images may be searched for using the information about the patient. The information about the patient may include the patient's name, the patient's ID, the patient's phone number, or a combination thereof, and may further include various other types of information about the patient, e.g., patient's address, patient's fingerprint, etc.

Radiography conditions may depend on the kind of an X-ray imaging apparatus being used to perform the radiography. Radiography conditions according to the kind of an X-ray imaging apparatus will be described in more detail, below.

In a general X-ray imaging apparatus, radiography conditions may include a tube voltage, a tube current, and a radiography time.

In a tomosynthesis X-ray imaging apparatus for photographing the chest, radiography conditions may include a tube voltage, a tube current, a radiography angular range, and a radiography location. The radiography angular range is a range within which the X-ray generator 110 rotates with respect to the object 30. The radiography location is a location at which the X-ray generator 110 irradiates X-rays onto the object 30 within the radiography angular range. The radiography location may depend on an interval in which the X-ray generator 110 moves.

In a tomosynthesis X-ray imaging apparatus for photographing a breast, radiography conditions may include a tube voltage, a tube current, a radiography angular range, a radiography location, and a degree of pressure.

The storage unit 160 stores the above-mentioned data and may be a volatile memory, a non-volatile memory, a hard disk, an optical disk, or a combination thereof. However, the storage unit 160 is not limited to the above-mentioned types of storage units, and may be an arbitrary storage device well-known in the art.

The controller 140 may connect and control the individual components in the X-ray imaging apparatus 100.

For example, the controller 140 may control movements of the X-ray generator 110 and/or the X-ray detector 120. More specifically, if the X-ray generator 110 moves manually or automatically, the controller 140 may move the X-ray detector 120 while keeping the X-ray detector 120 facing the X-ray generator 110.

As another example, if information about a patient is input through the input unit 131, the controller 140 may search for previous X-ray images related to information about the patient in the storage unit 160 and previous radiography conditions related to the information about the patient in the storage unit 160. The previous X-ray images may be 2D projection images or 2D reprojection images acquired upon previous radiography.

If neither previous X-ray images nor previous radiography conditions related to the information about the patient are found, the controller 140 may control the X-ray generator 110 to irradiate X-rays onto the object 30 according to radiography conditions set by an operator or according to arbitrary radiography conditions.

If previous X-ray images and previous radiography conditions related to the information about the patient are found, the controller 140 may set radiography conditions for a main-shot based on the found previous X-ray images and the found previous radiography conditions.

For example, the controller 140 may control the image processor 150 to analyze the quality of the previous X-ray images (e.g., 2D projection images or 2D reprojection images). If analysis on the quality of the previous X-ray images is completed, the controller 140 may adjust the previous radiography conditions based on the results of the quality analysis such that an X-ray image having better quality than the previous X-ray images can be acquired, and then the controller 140 may set the adjusted radiography conditions to radiography conditions for a main-shot. Thereafter, the controller 140 may control the X-ray generator 110 or both the X-ray generator 110 and the X-ray detector 120 to irradiate X-rays onto the object 30 according to the radiography conditions for the main-shot.

As another example, the controller 140 may control the image processor 150 to analyze the quality of 3D volume data. If the quality of 3D volume data is analyzed, the controller 140 may adjust the previous radiography conditions based on the results of the quality analysis such that 3D volume data having better quality than the previous 3D volume data can be acquired. Then, the controller 140 may set the adjusted radiography conditions to radiography conditions for a main-shot. Thereafter, the controller 140 may control the X-ray generator 110 or both the X-ray generator 110 and the X-ray detector 120 to irradiate X-rays onto the object 30 according to the radiography conditions for the main-shot.

As another example, the controller 140 may take a pre-shot according to the previous radiography conditions, compare the quality of an X-ray image acquired by the pre-shot to the quality of the previous X-ray images, and set radiography conditions for a main-shot based on the results of the comparison. Thereafter, the controller 140 may control the X-ray generator 110 or both the X-ray generator 110 and the X-ray detector 120 to irradiate X-rays onto the object 30 according to the radiography conditions for the main-shot.

Figure 11:
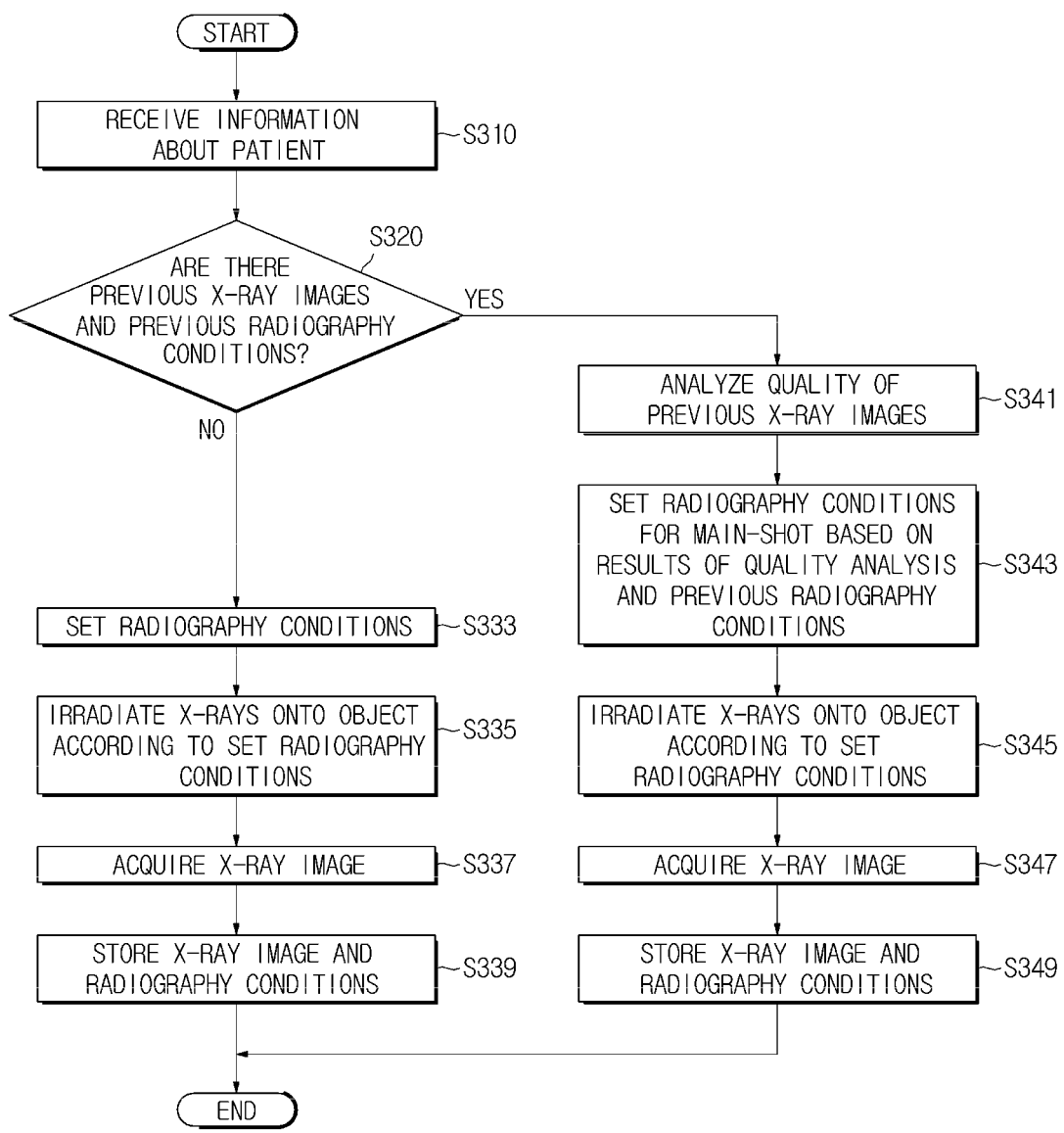
FIG. 11 is a flowchart of a control method of a general X-ray imaging apparatus, according to an exemplary embodiment.

FIG. 11 is a flowchart of a control method of a general X-ray imaging apparatus 100, according to an exemplary embodiment.

Referring to FIGS. 6 and 11, if information about a patient is input through the input unit 131 at operation S310, it may be determined whether there are previous X-ray images and previous radiography conditions related to the information about the patient at operation S320.

If neither previous X-ray images nor previous radiography conditions related to the information about the patient are found ("NO" in operation S320), radiography conditions may be set according to commands input by an operator at operation S333. For example, a tube voltage, a tube current, and a radiography time may be set as radiography conditions.

Thereafter, X-rays may be irradiated onto the object 30 according to the radiography conditions at operation S335.

Then, the X-rays transmitted through the object 30 may be converted into electrical signals by the X-ray detector 120, and an X-ray image may be acquired from the electrical signals at operation S337. Since the X-ray imaging apparatus 100 is a general X-ray imaging apparatus, the X-ray image acquired in operation S337 may be a 2D projection image.

The X-ray image acquired in operation S337 and the radiography conditions set in operation S333 may be stored in the storage unit 160, together with the information about the patient, at operation S339.

If previous X-ray images and previous radiography conditions related to the information about the patient are found ("YES" in operation S320), the quality of the previous X-ray images may be analyzed by the analyzer 157 of the image processor 150 at operation S341). For example, at least one of contrast, spatial resolution, SNR, NPS, MTF, and DQE of the previous X-ray images may be analyzed. The results of the quality analysis on the previous X-ray images may be provided to the controller 140.

Thereafter, radiography conditions for a main-shot may be set based on the results of the quality analysis on the previous X-ray images and the previous radiography conditions at operation S343). Operation S343 may include an operation of adjusting the previous radiography conditions in order to acquire an X-ray image having better quality than a quality of the previous X-ray images, and an operation of setting the adjusted radiography conditions to radiography conditions for a main-shot.

If the radiography conditions for the main-shot are set, X-rays may be irradiated onto the object 30 according to the radiography conditions for the main-shot at operation S345.

The X-rays irradiated onto the object 30 may be converted into electrical signals by the X-ray detector 120, and an X-ray image may be acquired from the electrical signals at operation S347). Since the X-ray imaging apparatus 100 is a general X-ray imaging apparatus, the X-ray image acquired in operation S347 may be a 2D projection image.

The X-ray image acquired in operation S347, and the radiography conditions for the main-shot set in operation S343, may be stored in the storage unit 160, together with the information about the patient, at operation S349.

Figure 12:
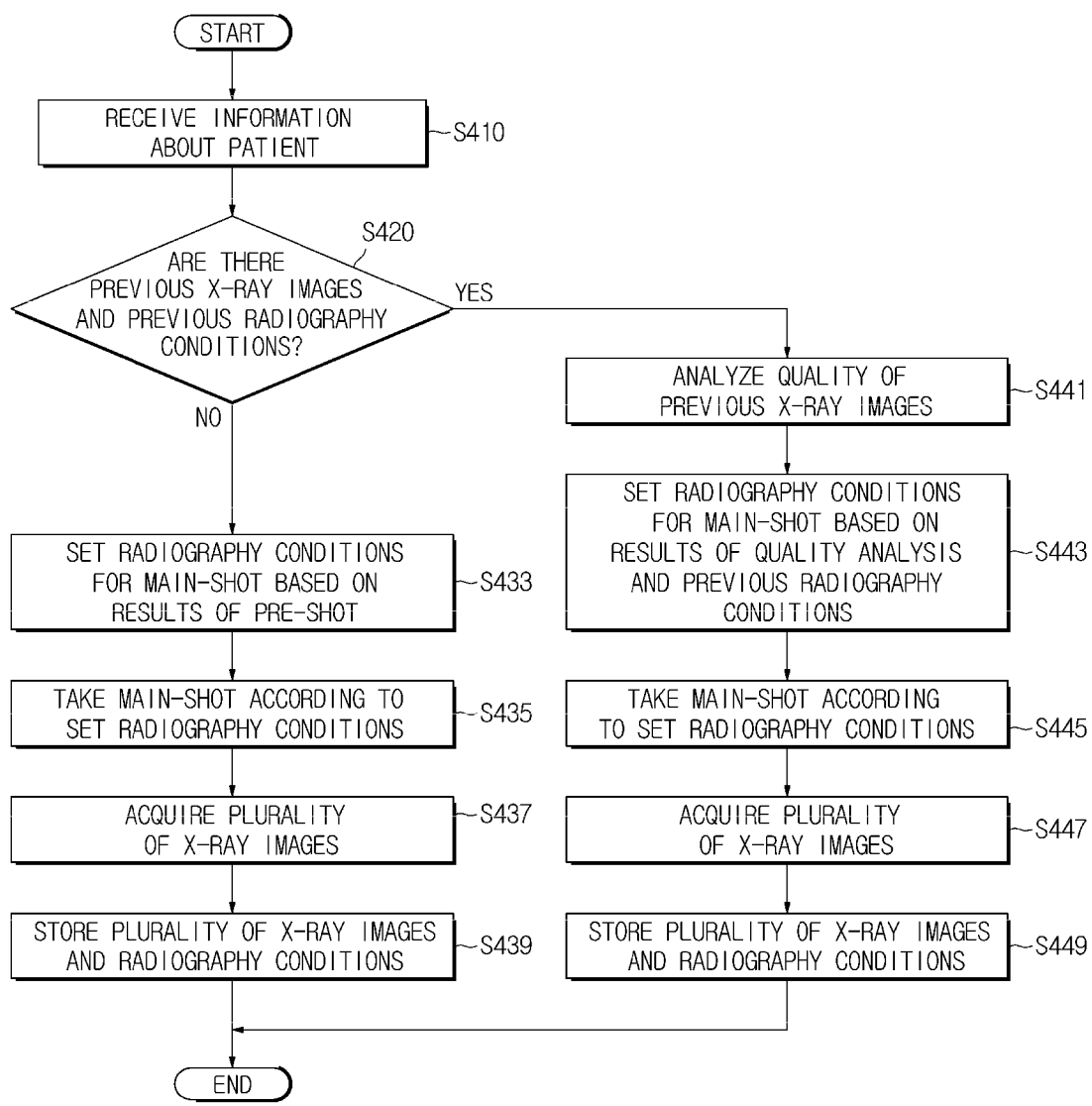
FIG. 12 is a flowchart of a control method of a tomosynthesis X-ray imaging apparatus, according to an exemplary embodiment.

FIG. 12 is a flowchart of a control method of a tomosynthesis X-ray imaging apparatus, according to an exemplary embodiment.

Referring to FIGS. 6 and 12, if information about a patient is input through the input unit 131 at operation S410, it may be determined whether there are previous X-ray images and previous radiography conditions related to the information about the patient at operation S420. The determination may be done by the controller 140.

If neither previous X-ray images nor previous radiography conditions related to the information about the patient are found ("NO" in operation S420), radiography conditions for a main-shot may be set based on the results of a pre-shot at operation S433. Operation S433 may include a pre-shot operation of irradiating a low dose of X-rays onto an object 30 one time, and an operation of setting radiography conditions for a main-shot based on an X-ray image acquired by the pre-shot.

When a chest tomosynthesis X-ray imaging operation is performed, radiography conditions for a main-shot may include a tube voltage, a tube current, a radiography angular range, and a radiography location. When a breast tomosynthesis X-ray imaging operation is performed, radiography conditions for a main-shot may include a tube voltage, a tube current, a radiography angular range, a radiography location, and a degree of pressure. It is understood that radiography conditions other than those listed above may also be used according to other exemplary embodiments.

After radiography conditions for a main-shot are set, a main-shot may be taken according to the radiography conditions at operation S435. That is, X-rays may be irradiated onto the object 30 at different locations.

Thereafter, the X-rays transmitted through the object 30 may be converted into electrical signals by the X-ray detector 120, and a plurality of X-ray images may be acquired from the electrical signals at operation S437. Since the X-ray imaging apparatus 100 is a tomosynthesis X-ray imaging apparatus, the X-ray images acquired in operation S437 may be a plurality of 2D projection images.

The plurality of X-ray images acquired in operation S437 and the radiography conditions set in operation S433 may be stored in the storage unit 160, together with the information about the patient, at peration S439.

If previous X-ray images and previous radiography conditions related to the information about the patient are found ("YES" in operation S420), the quality of the previous X-ray images may be analyzed by the analyzer 157 of the image processor 150 at operation S441. For example, at least one of contrast, spatial resolution, a SNR, a NPS, a MTF, and a DQE of the previous X-ray images may be analyzed. The results of the quality analysis on the previous X-ray images may be provided to the controller 140.

Thereafter, radiography conditions for a main-shot may be set based on the results of the quality analysis on the previous X-ray images and the previous radiography conditions at operation S443. Operation S443 may include an operation of adjusting the previous radiography conditions so that X-ray images having better quality than a quality of the previous X-ray images can be acquired, and an operation of setting the adjusted radiography conditions to radiography conditions for a main-shot.

After the radiography conditions for the main-shot are set, a main-shot may be taken according to the radiography conditions for the main-shot at operation S445. That is, X-rays may be irradiated onto the object 30 at different locations.

Then, the X-rays transmitted through the object 30 may be converted into electrical signals by the X-ray detector 120, and a plurality of X-ray images may be acquired from the electrical signals at operation S447. Since the X-ray imaging apparatus is a tomosynthesis X-ray imaging apparatus, the X-ray images acquired in operation S447 may be a plurality of 2D projection images.

The plurality of X-ray images acquired in operation S447 and the radiography conditions set in operation S443 may be stored in the storage unit 160, together with the information about the patient, at operation S449.

Figure 13:
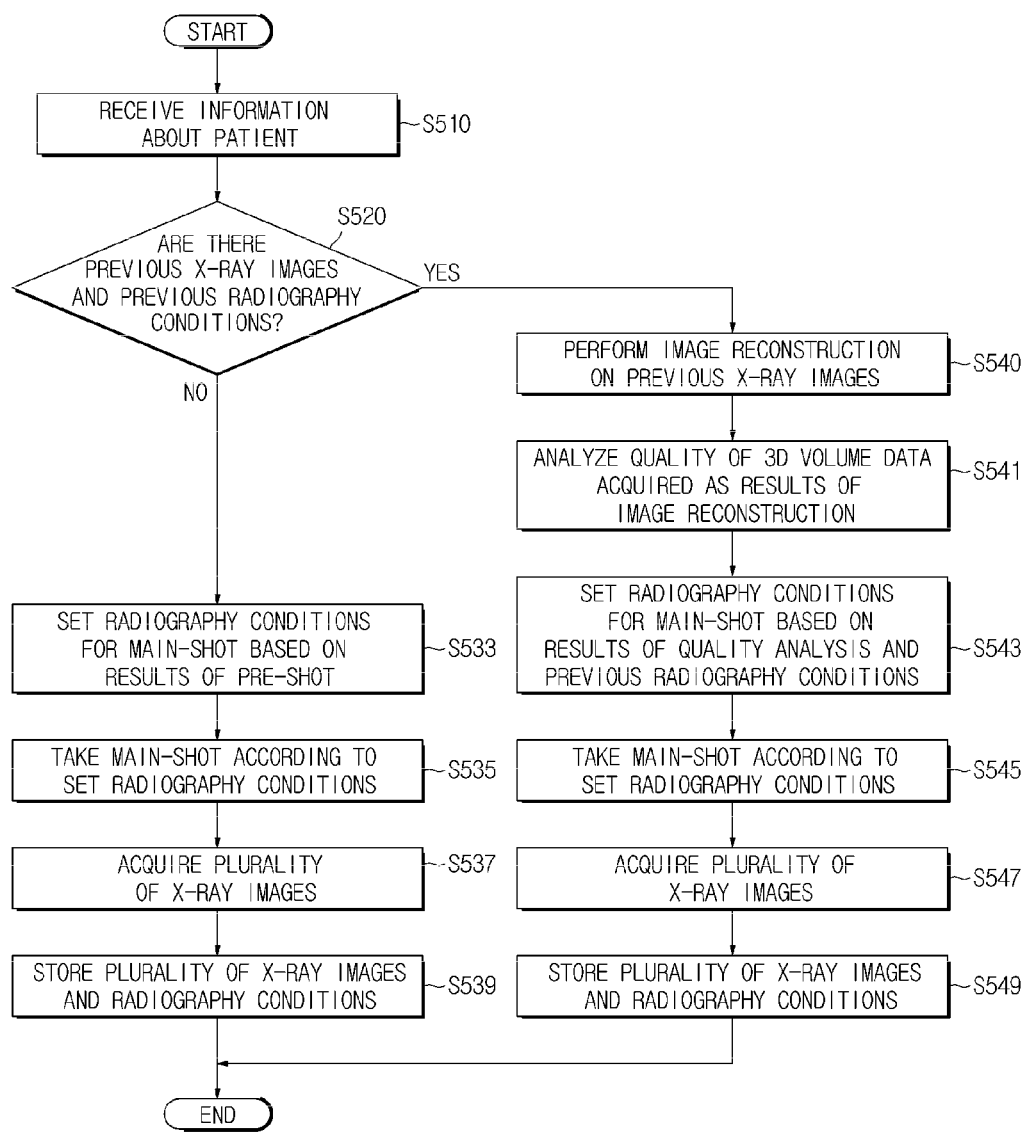
FIG. 13 is a flowchart of a control method of a tomosynthesis X-ray imaging apparatus, according to another exemplary embodiment.

FIG. 13 is a flowchart of a control method of a tomosynthesis X-ray imaging apparatus, according to another exemplary embodiment.

Referring to FIGS. 6 and 13, if information about a patient is input through the input unit 131 at operation S510, it may be determined whether there are previous X-ray images and previous radiography conditions related to the information about the patient at operation S520. The determination may be done by the controller 140.

If neither previous X-ray images nor previous radiography conditions related to the information about the patient are found ("NO" in operation S520), radiography conditions for a main-shot may be set based on the results of a pre-shot at operation S533. Operation S533 may include a pre-shot operation of irradiating a low dose of X-rays onto an object 30 one time, and an operation of setting radiography conditions for a main-shot based on an X-ray image acquired by the pre-shot.

If radiography conditions for a main-shot are set, a main-shot may be taken according to the radiography conditions for the main-shot at operation S535). That is, X-rays may be irradiated onto the object 30 at different locations.

Whenever X-rays are irradiated onto the object 30, the X-rays transmitted through the object 30 may be converted into electrical signals by the X-ray detector 120, and a plurality of X-ray images may be acquired from the electrical signals at operation S537).

The plurality of X-ray images acquired in operation S537 and the radiography conditions set in operation S533 may be stored in the storage unit 160, together with the information about the patient, at operation S539.

Meanwhile, if previous X-ray images and previous radiography conditions related to the information about the patent are found ("YES" in operation S520), image reconstruction may be performed on the previous X-ray images by the image reconstructing unit 153 of the image processor 150 at operation S540).

If 3D volume data is acquired as the result of the image reconstruction, the 3D volume data may be analyzed by the analyzer 157 of the image processor 150 at operation S541. For example, the frequency of the 3D volume data may be analyzed. The results of the quality analysis on the 3D volume data may be provided to the controller 140.

Thereafter, radiography conditions for a main-shot may be set based on the results of the quality analysis on the 3D volume data and the previous radiography conditions at operation S543). Operation S543 may include an operation of adjusting the previous radiography conditions in order to acquire X-ray images having better quality than a quality of the previous X-ray images, and an operation of setting the adjusted radiography conditions to radiography conditions for a main-shot.

After radiography conditions for a main-shot are set, a main-shot may be taken according to the radiography conditions for the main-shot at operation S545. That is, X-rays may be irradiated onto the object 30 at different locations.

Whenever X-rays are irradiated onto the object 30, the X-rays transmitted through the object 30 may be converted into electrical signals by the X-ray detector 120, and a plurality of X-ray images, specifically, a plurality of 2D projection images, may be acquired from the electrical signals at peration S547.

The X-ray images acquired in operation S547 and the radiography conditions set in operation S543 may be stored in the storage unit 160, together with the information about the patient, at operation S549.

Figure 14:
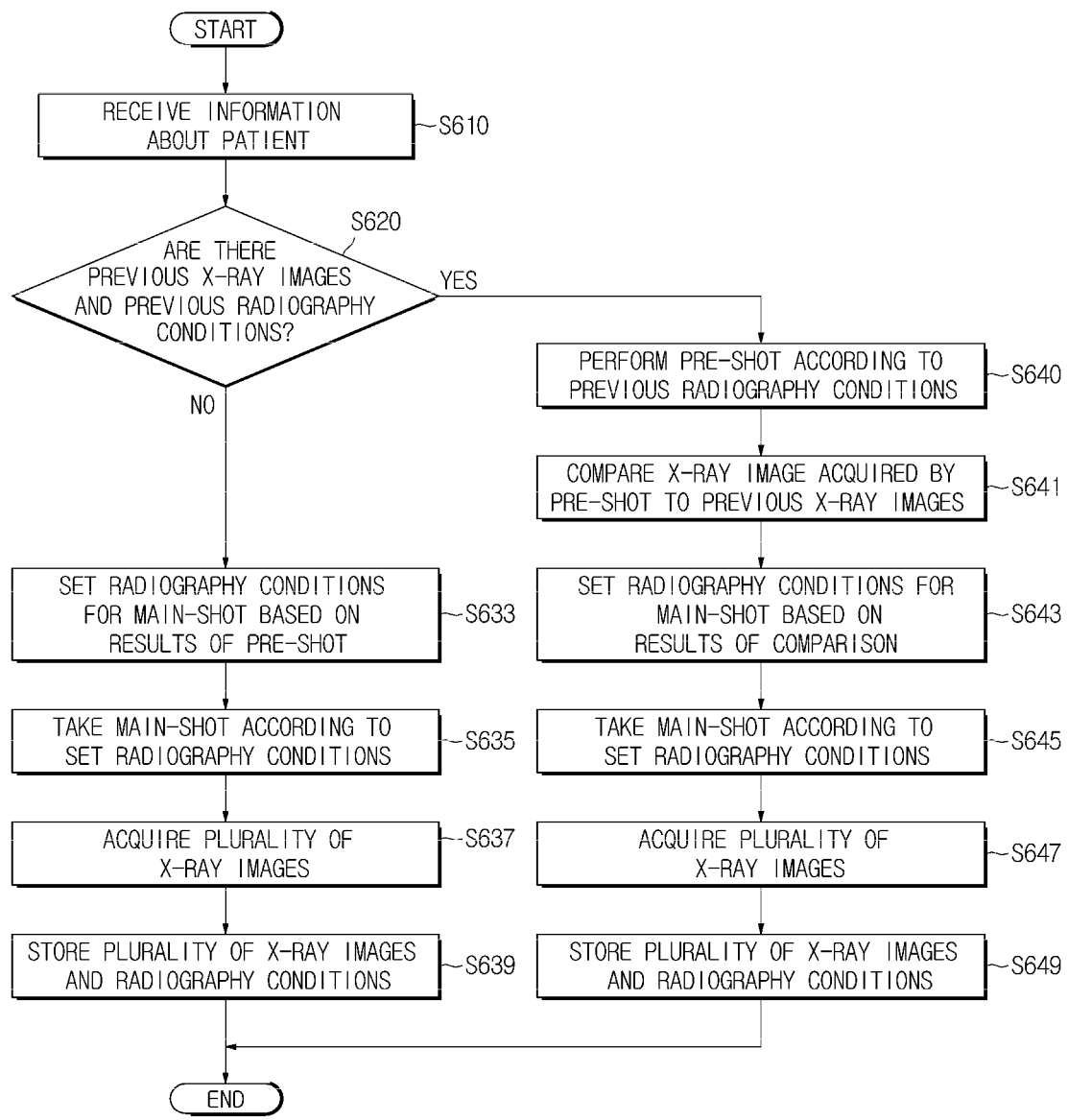
FIG. 14 is a flowchart of a control method of a tomosynthesis X-ray imaging apparatus, according to another exemplary embodiment.

FIG. 14 is a flowchart of a control method of a tomosynthesis X-ray imaging apparatus, according to another exemplary embodiment.

If information about a patient is input through the input unit 131 at operation S610, it may be determined whether there are previous X-ray images and previous radiography conditions related to the information about the patient at operation S620. The determination may be done by the controller 140.

If neither previous X-ray images nor previous radiography conditions related to the information about the patient are found ("NO" in operation S620), radiography conditions for a main-shot may be set based on the results of a pre-shot at operation S633. Operation S633 may include a pre-shot operation of irradiating a low dose of X-rays onto an object 30 one time, and an operation of setting radiography conditions for a main-shot based on an X-ray image acquired through the pre-shot.

After radiography conditions for a main-shot are set, a main-shot may be taken according to the radiography conditions for the main-shot at operation S635. That is, X-rays may be irradiated onto the object 30 at different locations.

Whenever X-rays are irradiated onto the object 30, the X-rays transmitted through the object 30 may be converted into electrical signals by the X-ray detector 120, and a plurality of X-ray images may be acquired from the electrical signals at operation 637.

The plurality of X-ray images acquired in operation S637 and the radiography conditions set in operation S633 may be stored in the storage unit 160, together with the information about the patient, at operation S639.

If previous X-ray images and previous radiography conditions related to the information about the patient are found ("YES" in operation S620), a pre-shot may be taken according to the previous radiography conditions at operation S640. That is, X-rays may be irradiated one time onto the object 30 according to the previous radiography conditions.

Thereafter, an X-ray image acquired by the pre-shot may be compared to the previous X-ray images at operation S641. More specifically, the quality of the X-ray image acquired by the pre-shot and the quality of the previous X-ray images may be analyzed by the analyzer 157, and the results of the quality analysis may be compared to each other. The reason for comparing the quality of the X-ray image acquired by the pre-shot to the quality of the previous X-ray images is because the quality of the X-ray image acquired by the pre-shot can be different from the quality of the previous X-ray images, even though the X-ray images have been acquired under the same radiography conditions. The results of the quality comparison between the X-ray images may be provided to the controller 140.

Thereafter, radiography conditions for a main-shot may be set based on the results of the quality comparison between the X-ray images at operation S643. The operation S643 may include an operation of adjusting the previous radiography conditions in order to acquire an X-ray image having better quality than a quality of the previous X-ray images, and an operation of setting the adjusted radiography conditions to radiography conditions for a main-shot.

After the radiography conditions for the main-shot are set, a main-shot may be taken according to the radiography conditions for the main-shot at operation S645. That is, X-rays may be irradiated onto the object 30 at different locations.

Whenever X-rays are irradiated onto the object 30, the X-rays transmitted through the object 30 may be converted into electrical signals by the X-ray detector 120, and a plurality of X-ray images may be acquired from the electrical signals at operation S647.

The plurality of X-ray images acquired in operation S647 and the radiography conditions set in operation S643 may be stored in the storage unit 160, together with the information about the patient, at operation S649). The plurality of X-ray images and the radiography conditions stored in the storage unit 160 may be referred to in order to set radiography conditions for a next shot.

Although a few exemplary embodiments have been shown and described, it would be appreciated by those skilled in the art that changes may be made in these exemplary embodiments without departing from the principles and spirit of the disclosure, the scope of which is defined in the claims and their equivalents.

What is claimed is:

1. An X-ray imaging apparatus comprising:
    an X-ray generator;
    an input device configured to receive information about an object;
    a controller configured to conduct a search for a previously obtained X-ray image related to the information about the object and a previously set radiography condition related to the information about the object, and to set a radiography condition for a main-shot based on a result of the search; and
    an image processor configured to analyze a quality of the previously obtained X-ray image,
    wherein the controller is further configured to perform a pre-shot by controlling the X-ray generator to irradiate a low dose of X-rays onto the object, if neither the previously obtained X-ray image nor the previously set radiography condition related to the information about the object are found, and to set the radiography condition for the main-shot based on an X-ray image acquired by the pre-shot.

2. The X-ray imaging apparatus according to claim 1, wherein the image processor is configured to analyze at least one among contrast, spatial resolution, a Signal to Noise Ratio (SNR), a Noise Power Spectrum (NPS), a Modulation Transfer Function (MTF), and a Detective Quantum Efficiency (DQE) of the previously obtained X-ray image.

3. The X-ray imaging apparatus according to claim 1, wherein the previously obtained X-ray image is at least one of a 2-Dimensional (2D) projection image acquired by irradiating X-rays onto an object and a 2-Dimensional (2D) reprojection image acquired by performing volume rendering on 3-Dimensional (3D) volume data reconstructed from a plurality of 2-Dimensional (2D) projection images.

4. The X-ray imaging apparatus according to claim 1, wherein the controller is further configured to adjust the previously set radiography condition based on the analyzed quality of the previously obtained X-ray image, set the adjusted previously set radiography condition as the radiography condition for the main-shot, and control X-ray generator to irradiate X-rays onto the object according to the radiography condition for the main-shot.

5. The X-ray imaging apparatus according to claim 1, wherein the controller is configured to adjust the previously set radiography condition based on the analyzed quality of the previously obtained X-ray image, set the adjusted previously set radiography condition as the radiography condition for the main-shot, and irradiate X-rays onto the object at different locations according to the radiography condition for the main-shot to perform the main-shot.

6. The X-ray imaging apparatus according to claim 1, wherein the image processor is further configured to perform image reconstruction on the previously obtained X-ray image, and to analyze a quality of 3-Dimensional (3D) volume data acquired as a result of the image reconstruction.

7. The X-ray imaging apparatus according to claim 6, wherein the controller is configured to adjust the previously set radiography condition based on the analyzed quality of the 3D volume data, set the adjusted previously set radiography condition as the radiography condition for the main-shot, and irradiate X-rays onto the object at different locations according to the radiography condition for the main-shot to perform the main-shot.

8. The X-ray imaging apparatus according to claim 1, wherein the image processor is further configured to make a comparison between a quality of an X-ray image acquired by the pre-shot obtained by irradiating X-rays onto the object one time according to the previously set radiography condition to the quality of the previously obtained X-ray image.

9. The X-ray imaging apparatus according to claim 8, wherein the controller is configured to adjust the previously set radiography condition based on results of the comparison between the quality of the X-ray image acquired by the pre-shot to the quality of the previously obtained X-ray image, and set the adjusted previously set radiography condition as the radiography condition for the main-shot.

10. The X-ray imaging apparatus according to claim 1, further comprising a storage configured to store an X-ray image acquired by irradiating X-rays onto the object according to the radiography condition for the main-shot, the radiography condition for the main-shot, and the information about the object.

11. The X-ray imaging apparatus according to claim 1, further comprising a storage configured to store a plurality of X-ray images acquired by irradiating X-rays onto the object at different locations according to the radiography condition for the main-shot, the radiography condition for the main-shot, and the information about the object.

12. A control method to control an X-ray imaging apparatus, the control method comprising:
receiving information about an object;
searching for a previously obtained X-ray image and a previously set radiography condition related to the information about the object;
setting a radiography condition for a main-shot based on a result of the searching if the previously obtained X-ray image and the previous set radiography condition related to the information about the object are found; and
performing a pre-shot by irradiating a low dose of X-rays onto the object, if neither the previously obtained X-ray image nor the previously set radiography condition related to the information about the object are found, and setting the radiography condition for the main-shot based on an X-ray image acquired by the pre-shot,
wherein the setting of the radiography condition for the main-shot comprises:
analyzing a quality of the previously obtained X-ray image;
adjusting the previously set radiography condition based on a result of the analyzing of the quality of the previously obtained X-ray image; and
setting the adjusted previously set radiography condition as the radiography condition for the main-shot.

13. An X-ray imaging apparatus comprising:
an X-ray generator;
a storage configured to store a previously obtained X-ray image and a previously set radiography condition used to obtain the previously obtained X-ray image;
an image processor configured to analyze a quality of the previously obtained X-ray image and thereby output a quality analysis result; and
a controller configured to selectively adjust the previously set radiography condition according to the quality analysis result and use the adjusted radiography condition to acquire a current X-ray image,
wherein the controller is further configured to perform a pre-shot by controlling the X-ray generator to irradiate a low dose of X-rays onto an object, if neither the previously obtained X-ray image nor the previously set radiography condition are found, and to set a radiography condition for a main-shot based on an X-ray image acquired by the pre-shot.

14. The X-ray imaging apparatus according to claim 13, wherein the storage is further configured to store information related to a subject of the previously obtained X-ray image, and wherein the controller is configured to search for the previously obtained X-ray image and the previously set radiography condition based on the information.

15. The X-ray imaging apparatus according to claim 14, wherein the subject is the object, and wherein the information comprises at least one of a name of the object and a telephone number of the object.

16. The X-ray imaging apparatus according to claim 15, wherein the controller is configured to adjust the previously set radiography condition such that the current X-ray image is acquired at a higher quality than the quality of the previously obtained X-ray image, according to the quality analysis result.

* * * * *